Figure 1:
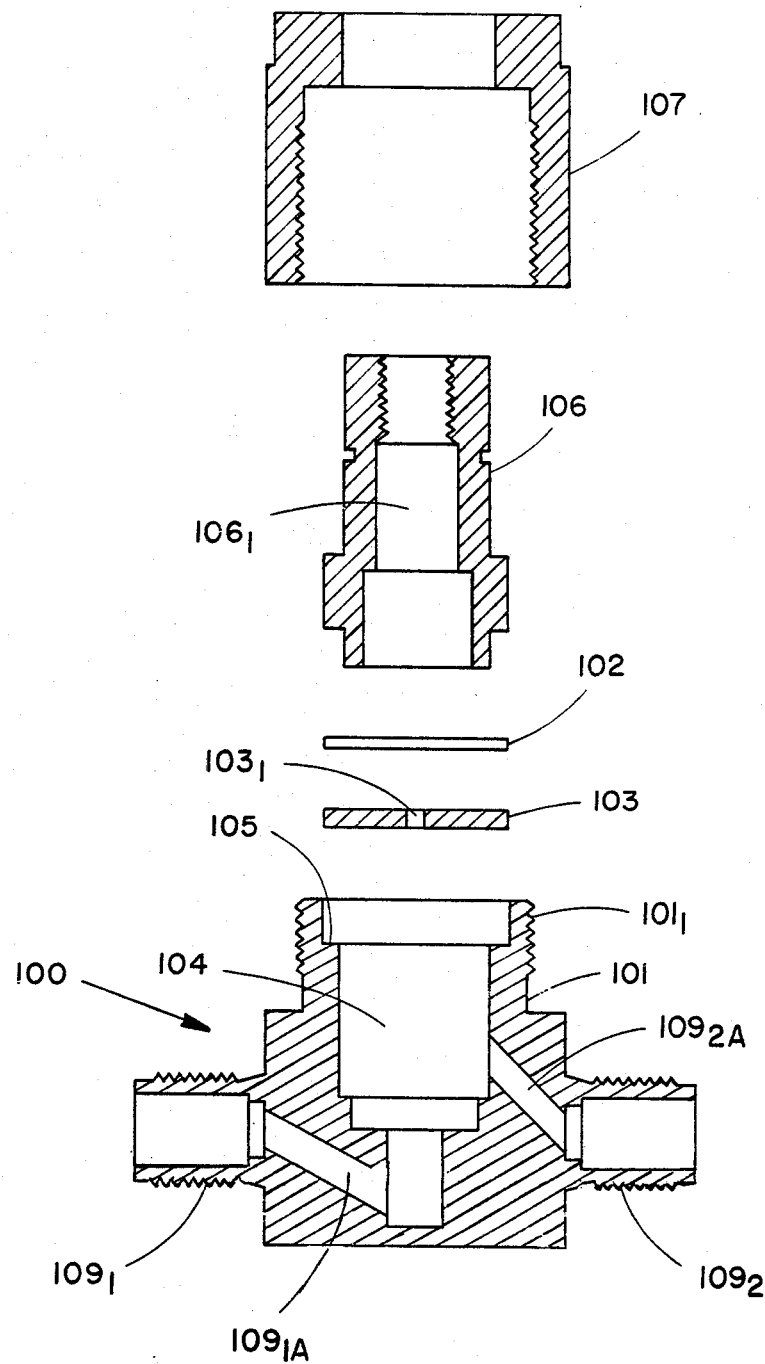

United States Patent [19]

Daigle

[11] Patent Number: 4,806,315

[45] Date of Patent: Feb. 21, 1989

[54] WATER VAPOR ADDITION FOR GAS CHROMATOGRAPHY, AND GAS CHROMATOGRAPHS

[75] Inventor: Emanuel L. Daigle, Gonzales, La.

[73] Assignee: The Dow Chemical Company, Midland, Mich.

[21] Appl. No.: 69,070

[22] Filed: Jul. 2, 1987

[51] Int. Cl.$^4$ .............................................. G01N 30/02
[52] U.S. Cl. ................................. 422/89; 73/61.1 C; 436/168; 436/150
[58] Field of Search ................................ 422/68–70, 422/96, 97, 89; 210/198.2, 321.1, 649, 656, 659; 436/168, 175–178, 150; 73/61.1 C

[56] References Cited

U.S. PATENT DOCUMENTS 4,442,217  4/1984  Deans ..................................... 422/89
4,533,518  8/1985  Hanaoka et al. ..................... 422/70
4,584,276  4/1986  Hanaoka et al. ..................... 436/150

Primary Examiner—Barry S. Richman
Assistant Examiner—I. J. Wallen
Attorney, Agent, or Firm—Llewellyn A. Proctor

[57] ABSTRACT

The disclosure relates to improvements in the art of gas chromatography, and gas chromatographs containing a detector operated on the thermal conductivity principle. In the conventional gas chromatograph, a pair of resistance filaments constitutes an opposite arm of a Wheatstone bridge, and each of two pairs of filaments provides a reference side and a measuring side, respectively, across which a carrier gas can be flowed and the bridge balanced. A moisture-containing sample can be input and transported via carrier gas through a circuit to a substrate filled column and the moisture and other components of the sample separated according to their different affinities for the column substrate. The sample constituents elute from the column in characteristic sequence as elution bands diluted with carrier gas. The column effluent, in such system, can be flowed across the pair of resistance filaments constituting the measuring side of the bridge and the bridge unbalanced to create a bridge-inbalance signal which can be processed as output data indicative of the moisture contained in the sample. The present invention is based on the discovery that a constant and continuous amount of water vapor from an extraneous source can be added as via water vapor addition means to the carrier gas input to the system sufficient to suppress the normal tendency of the moisture contained in the sample to wet and adhere to gas chromatograph surfaces with which the moisture-containing sample is contacted.

9 Claims, 3 Drawing Sheets

WATER VAPOR ADDITION FOR GAS CHROMATOGRAPHY, AND GAS CHROMATOGRAPHS

FIELD OF THE INVENTION

This invention relates to improvements in gas chromatography, and gas chromatographs. In particular, it relates to apparatus and process for the more effective qualitative and quantitative chemical analysis of the water component of a water-containing sample.

BACKGROUND

Gas chromatography is a well established technique for qualitative and quantitative chemical analysis, and gas chromatographs, i.e. G.C.'s, are used worldwide by the industrial, scientific, medical and academic communities. In G.C. analysis, a measured volume of a sample, or specimen, is injected into a substrate filled column and carried therethrough by a continuous flow of an inert or non-reactive carrier gas, e.g. helium, argon, nitrogen and hydrogen. The individual components, or constituents of the sample are separated in the column in accordance with their differing affinities for the substrate employed in the column. The components emerge from the column in characteristic sequence, as elution bands diluted with the carrier gas, and each is monitored by a detector, i.e. a thermal-conductivity detector or flame ionization detector. The detector-output signal is processed electronically, the data output, and graphically recorded. The different components of the sample are generally exhibited as chromatograms and appear in a sequence readily identifiable by their characteristic location on the chromatogram, and each is readily quantified by peak heights, or areas under the curve graphically drawn for a given component, or both.

Samples subjected to G.C. analysis often contain low concentrations of water, or moisture. Quite obviously in most situations it is also desirable, if not necessary, not only to properly identify but to ascertain the amount of water in the sample. Often samples are analyzed solely for the determination of water content. Unfortunately however, it is very difficult and often not possible to reliably determine the amount of water in a given sample by G.C. analysis, especially when the water is present in small and infinitesimal concentrations ranging, e.g., from about 1 to 100 parts per million (ppm), or less, based on the total weight of the sample. Characteristically, the water lags and tails on passage through the system so that the graphical trace representative of the detector-output signal for water can be read only with difficulty, if accurately read at all. Thus, characteristically, the widths of the H$_2$O peaks are drastically increased, and the chromatogram heights shortened, and tailed. This is because the water component of a sample tends to wet and adhere to surfaces within the G.C. and auxiliary components of the instrument with which it comes into contact, the moisture lagging and tailing through the instrument. Consequently, accurate analysis for water is impractical, and often virtually impossible: particularly where the water is present in the sample in small and infinitesimal concentrations.

OBJECTS

It is, accordingly, an object of this invention to provide improvements in gas chromatographs, and in the art of gas chromatography, for water analysis.

It is a particular object of this invention to provide apparatus and process for the repetitive, precise and accurate analysis of the water component of a water-containing sample, especially a sample wherein the water is present in concentrations measured in the microliter range, notably from about 1 to 100 ppm, and less, based on the total weight of the sample.

A specific object is to provide means, in terms of both apparatus and process, for the more precise and accurate quantitative measurement of the moisture content of a water-containing sample by G.C. analysis wherein the chromatographic output can be repetitively read as a sharp peak of narrow width accurately representative of the moisture contained within the sample.

THE INVENTION

These objects and others are achieved in accordance with the present invention embodying improvements in gas chromatographs or gas chromatograph systems, and gas chromatography, of the type containing a detector, or sensor, operated on the thermal conductivity principle characterized generally as a Wheatstone bridge. In such system, opposite arms of the bridge are constituted of a pair of filaments, each of two pairs of filaments providing a measuring side and a reference side, respectively, across both of which carrier gas can be simultaneously flowed and the bridge balanced. A moisture-containing sample can be input, e.g. from a sample loop, and transported via carrier gas to a substrate filled column and the moisture and other components of the sample separated according to their different affinities for the column substrate to emerge from the column in characteristic sequence as elution bands diluted with carrier gas. The column effluent, in such system, can be transported with carrier gas, and flowed across the pair of resistance filaments constituting the measuring side of the bridge and the bridge unbalanced to create a bridge-inbalance signal which can be processed, though ineffectively, as output data indicative of the moisture contained in the sample. The present invention is based on the discovery that water vapor from an extraneous source can be added as via water vapor addition means to carrier gas input to the system sufficient to suppress the normal tendency of the moisture component of the sample to wet and adhere to gas chromatograph surfaces as a consequence of which, with carrier gas flowing across both the reference side and the measuring side of the Wheatstone bridge detector element with the bridge balanced, the carrier gas from the column carrying the moisture-containing portion of the sample can be flowed across the measuring side of the bridge to produce bridge inbalance and a bridge-inbalance signal which can be processed as output data accurately indicative of the water content of the sample. The moisture content can be read with a precision and accuracy not characteristic of a gas chromatograph which does not include the addition of water vapor, or means for the addition of water vapor, to the gas chromatograph, or gas chromatograph system, as part of said combination.

It is necessary in the practice of this invention, for best results, to introduce a constant and continuous amount of water vapor into the carrier gas supplied to that portion of the G.C. providing a surface, or surfaces, with which the moisture-containing sample can contact after introduction into the G.C. The water vapor-containing carrier gas after introduction into the G.C. is thus contacted with all surfaces which the moisture-containing sample will contact in the path of flow between its point of introduction into the system and the measuring side of the bridge where analysis of the sample takes place. Contact is continued to wet the surface sufficiently, to suppress the normal tendency of the sample moisture to wet and adhere to this surface, or surfaces, as a consequence of which the moisture eluted from the moisture-containing sample and transported by the diluting carrier gas will not adhere to or be adsorbed upon these surfaces. Thus, the eluted moisture transported by the diluting carrier gas through the G.C. will be delivered to the measuring side of the balanced bridge for analysis as is normal for most non-aqueous components of a sample. Since, in conducting the analysis, it is necessary to first balance the Wheatstone bridge while conveying carrier gas to both the measuring side and the reference side of the bridge, it is preferable to also add water vapor to the carrier gas to both the measuring side and the reference side of the bridge. Suitably water vapor is added, as by water vapor injection means, at the point of supply of carrier gas to the system, and preferably the carrier gas to which the water vapor has been added is flowed in constant amount and continuously through a first circuit which contains a sample injection means and downstream eluting column and a second circuit which transports the carrier gas to the two sides of the bridge, viz. the measuring side and the reference side thereof. In such system, the moisture-containing sample can be injected at intervals via the sample injection means and carried by the carrier gas into the pre-wetted first circuit, the sample eluted in the column, and the column elution bands diluted with carrier gas conveyed to the measuring side of the bridge. The bridge in such system is balanced preferably by carrier gas of similar water vapor content introduced in constant and continuous amount via a second circuit across both the reference side and measuring side of the bridge. The output signal representative of the moisture content of the water-containing sample can be read with the precision and accuracy normal for non-aqueous sample components.

These and other features of the novel apparatus, and process, as well as its principle of operation will be better understood by reference to the following drawing and detailed description which makes reference to the drawing. In the drawing, similar numbers are used in the different figures to represent similar parts, or components, and subscripts are used with a given whole number to designate similar parts or components where a plurality of such parts or components are employed in the structure. Where a whole number is used in the text to designate parts or components present in the structure in number greater than one, the reference is intended in a generic sense.

Figure 2:
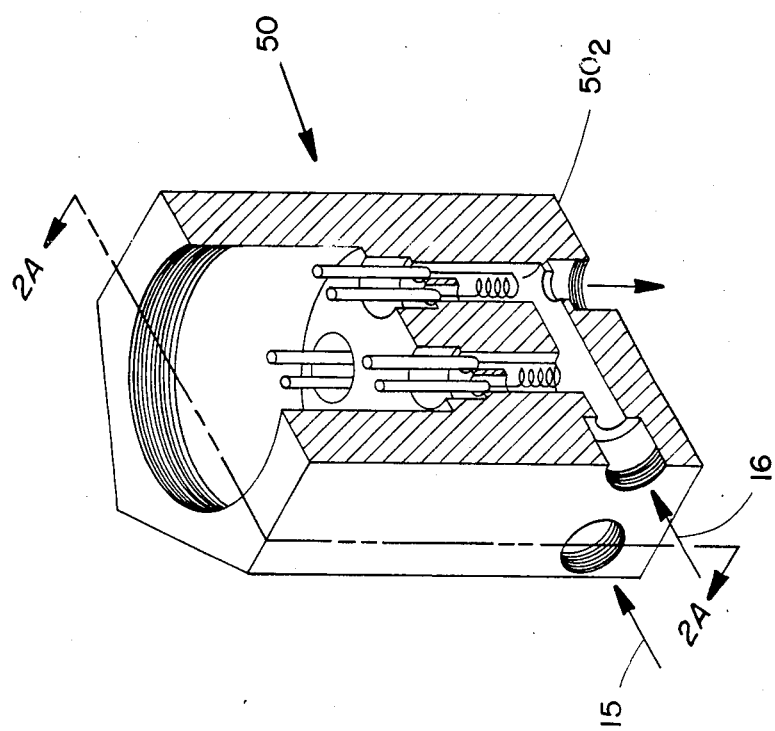
Figure 2A:
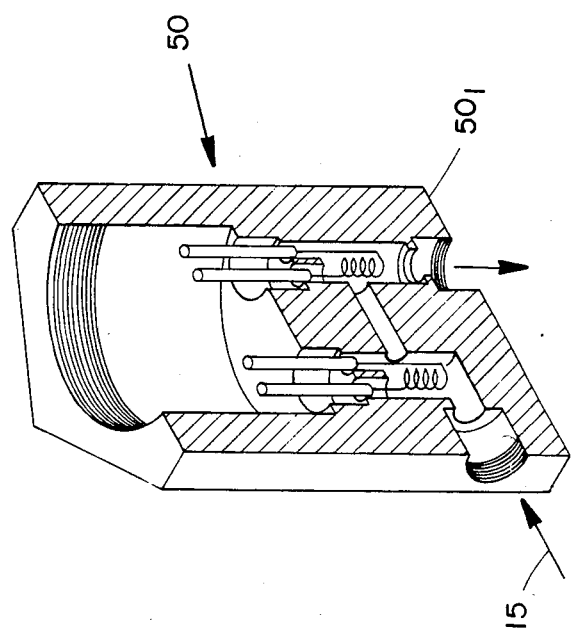

In the drawing:

FIG. 1 depicts a sectional elevation view of a water vapor addition module, in exploded fashion, for use in operative association with a water supply source and G.C.:

FIG. 2 depicts an isometric sectional view of a detector, housed in a block providing a Wheatstone bridge sensor which contains a passage to a reference side, and passage to a measuring side, to both of which a continuous flow of carrier gas can be input to flow across pairs of filament resistances constituting the opposite arms of the bridge: the reference side receiving carrier gas, and the measuring side receiving carrier gas and a column effluent consisting of carrier gas and eluting sample components:

FIG. 2A is a section taken through 2A—2A of FIG. 2: and

Figure 3:
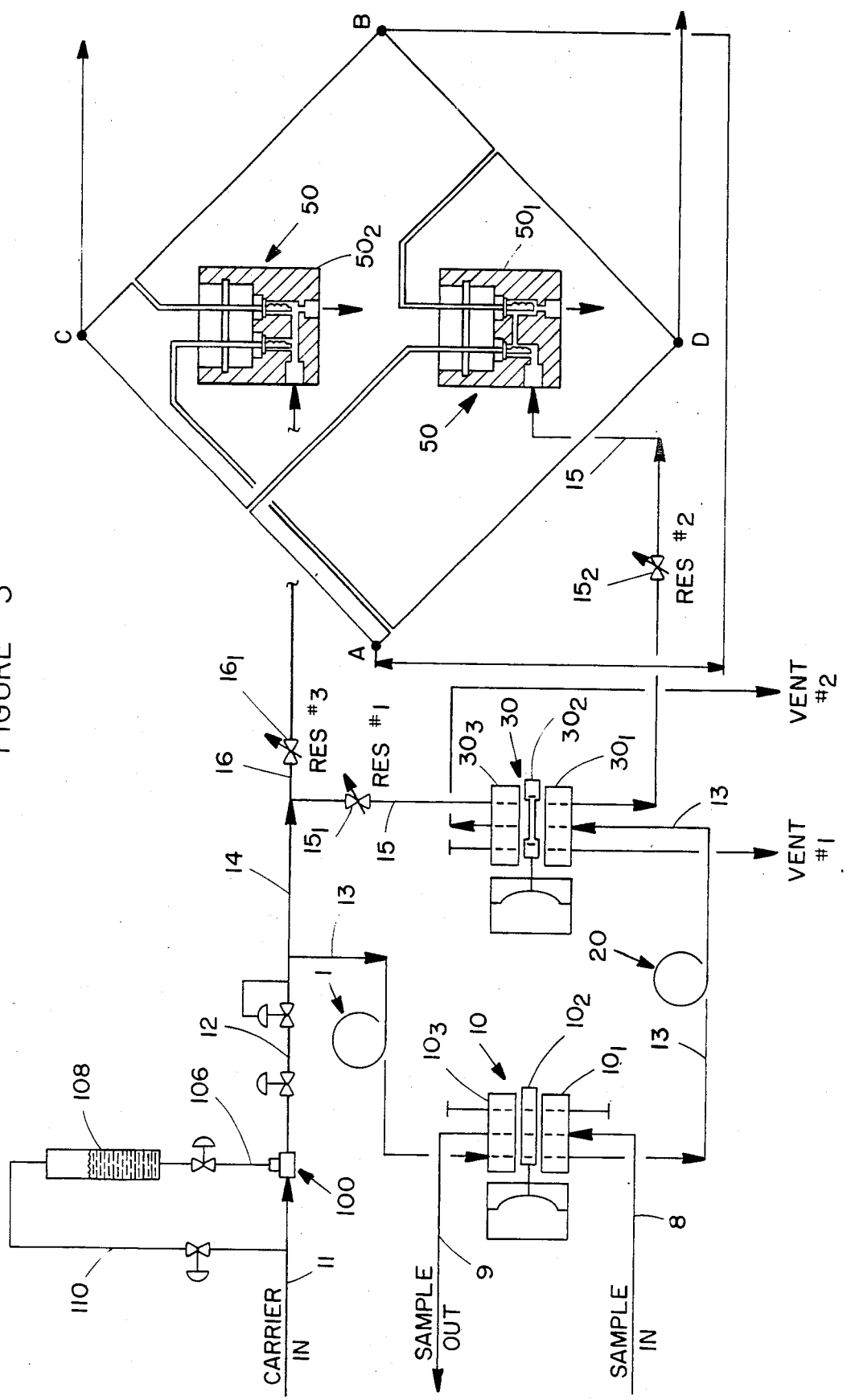

FIG. 3 depicts the water vapor addition module, water supply source, and G.C. in operative association, inclusive of heater lines, valving, sample inject means, column and thermal conductivity detector, the latter being illustrated functionally in terms of its two sides in a bridge circuit, though physically the detector is constituted in one piece and housed in a single block as illustrated in FIG. 2.

Referring first generally to FIG. 1, there is shown a preferred type of water vapor addition module 100 for use in continuously adding moisture from an extraneous source, e.g. a water-filled vessel 108 as subsequently described, to a carrier gas supplied to the G.C. With reference to FIG. 3, the water vapor addition module 100 is shown in combination with a pressurized water-filled vessel 108, the latter being mounted above the water addition module 100 for the supply of water vapor thereto via the line 106. Carrier gas is passed via line 11, preferably continuously and at a constant rate of flow, into the water vapor addition module 100, picks up water vapor in uniform amount therefrom on passage therethrough, and is then split into two streams: a first stream which is passed via line 13 through a first circuit to a heater 1 which heats the gas, through a sample inject, or sample injection valve 10, a column control or sample eject valve 30, then to the measuring side $50_1$ of detector block 50 and a second stream which after passage through line 14 is again split into two streams and passed via lines 15 and 16, respectively, through the sample eject valve 30 to the measuring side $50_1$, of the detector block 50 and reference side $50_2$ of the detector block 50, respectively. The first circuit with the water vapor-containing carrier gas being continuously passed therethrough maintains the inside surface of the lines and surfaces of the system between the sample inject valve 10, the point where the water-containing sample is intermittently injected via a sample loop 8, 9, and the measuring side $50_1$, of the detector 50 sufficiently wetted that the water component of said water-containing sample when introduced will not adhere on passage to these surfaces. With a water vapor-containing carrier gas of similar moisture content flowing via said second circuit through both the measuring side $50_1$, and resistance side $50_2$ of the detector 50 the bridge component of the detector can be balanced such that when the water-containing sample is injected via the sample inject valve 10 into line 13, fed into column 20 and the eluted moisture component of the sample passed through the measuring side $50_1$ of the detector 50 its moisture content is readily and rapidly read by the detector because the moisture is passed through the instrument without hold-up since there are no water adsorption sites to obstruct passage of the water component of the sample.

The details of the water vapor addition module 100 are best described by specific reference to FIG. 1 which depicts in detail its several components. The water vapor addition module 100 consists principally of a membrane housing 101 or hollow body providing a chamber 104 above which is supported a water permeable membrane 102. In assembled position, the permeable membrane 102 fits against the upper face of a washer 103 and these in turn are seated and supported in contiguous relationship above the chamber 104 resting upon the annular shoulders 105 formed by the larger of the pair of concentric vertically oriented openings within the upwardly projected externally threaded portion of said housing 101. The washer 103 supports and circumferentially seals the membrane 102 at its outer edges, and by proper selection of the internal diameter of the central opening therethrough the active surface area through which vapor or moisture is transmitted in to the chamber 104 is determined. The nature and composition of the material of which the membrane is constructed, its thickness and the diameter of the washer opening can thus be varied to supply the desired amount of vapor or moisture to the chamber 104 in constant and continuous amount. The lower end of the pipe segment 106 rests atop, and the wall thereof circumferentially covers the edges of the membrane 102. The pipe segment is, in turn, coupled with and supported atop the membrane housing 101 by means of the internally threaded locknut 107 which, in assembled position, is threadably engaged with external threads $101_1$, of the membrane housing 101. Moisture or vapor is supplied to chamber 104 of the membrane housing 101 via the vertically oriented channel $106_1$, from a water-containing vessel 108 supported above the water injection module 100 (FIG. 3). A liquid water interface rests against the upper face of the membrane 102, and moisture or vapor is conveyed to the chamber 104 via the central opening $103_1$ of washer 103 where it is picked up as a vapor by the carrier gas passing therethrough. Carrier gas introduced into chamber 104 via externally threaded inlet port $109_1$ will thus enter via passageway $109_{1A}$ to chamber 104, pick up moisture supplied from vessel 108 via pipe segment 106 and membrane 102, and the moisture-containing carrier gas will exit chamber 104 via passageway $109_{2A}$ and externally threaded outlet port $109_2$. With further specific reference to FIG. 3, carrier gas is input to inlet port $109_1$ of the water vapor addition module 100 via line 11, and output therefrom via outlet port $109_2$ via line 12. The pressure is equilibrated between water-containing vessel 108 and lines 11, 12 which convey the carrier gas through the water vapor addition module 100 via lines 106, 110.

Water permeable membranes per se are well known. Exemplary of water permeable membranes are, e.g., NAFION (Tradename of E. I. Dupont de Nemours & Co., Inc.), a perfluorosulfonate ionomer, polytetrafluoroethylene, fluorinated ethylenepropylene and the like. Dependent on the specific membrane employed, and the flow rate of the carrier gas, generally the diameter of membrane exposed to the carrier gas flowing through the chamber of the membrane housing will range in diameter from about 1/32 inch to about ½ inch, and more generally from about ⅛ inch to about ¼ inch.

In terms of apparatus, the water vapor addition module 100, water supply vessel 108 and connecting means are integrated with an entirely, presently conventional, G.C. system. The new combination, however, makes it possible to repetitively analyze a water-containing sample to determine its moisture content with a precision and accuracy not heretofore possible. This is based on the discovery that moisture from an extraneous source of supply can be input to the G.C. in amount sufficient to saturate and wet the inner surfaces of the instrument and its auxiliary components with which the carrier gas comes in contact such that on injection into the instrument of a moisture-containing specimen, or sample, the water component of the sample will be passed with the carrier gas through the instrument to the measuring side of the detector without adsorption upon instrument surfaces. As a result, the moisture of the sample will be eluted through the column, without adsorption on instrument surfaces and can now be properly processed by the measuring side of the detector, the detector-output signal for moisture processed without distortion, and the data recorded and read as are chromatograms representative of numerous other chemical species commonly analyzed by G.C.

The G.C. system, reference being made to Figure 3, thus includes a water supply circuit, or circuit containing the water vapor addition module 100 and water supply vessel 108. Carrier gas is introduced via line 11 into the water vapor addition module 100 picking up moisture therefrom prior to entry into line 12. The system further includes a first circuit, or sample supply circuit which includes a sample inject valve 10, a sample loop 8, 9, a column 20, and a sample eject valve 30 serially connected together through line 13. Carrier gas from line 12 now carrying water vapor picked up from the water vapor addition module 100 is thus split between lines 13, 14 flowing via line 13 through the sample inject valve 10, column 20, sample eject valve 30 and line 15 to the measuring side $50_1$ of the detector 50. The system moreover includes a branched circuit, or second circuit, whereby the water vapor-containing carrier gas is continuously passed via lines 12, 14 through lines 15, 16, respectively, to both the measuring side $50_1$ and the reference side $50_2$ of the detector 50. Thus, carrier gas is introduced via lines 12, 14, 16 to the reference side $50_2$ of the detector 50 and thereafter vented after passage across the reference filaments, and introduced via lines 12, 14, 15 to the measuring side $50_1$ of the detector 50 and then vented after passage across the measuring filaments.

The sample inject valve 10 can be one of several known designs, e.g. a multi-port slide valve of a type employed on the Model 6750 Process Gas Chromatograph System manufactured and marketed by Beckman Instruments, Inc. of Fullerton, Calif. In its de-energized mode the sample is flowed continuously through one of the ports of the slide $10_2$ not aligned with line 13. Thus, a water-containing sample which is to be analyzed is introduced via line 8 into the sample inject valve 10, the sample passing through an opening of the lower body portion $10_1$ and an opening of calibrated diameter and length within slide $10_2$ to egress via an opening of the upper body portion $10_3$ through line 9. Simultaneously, carrier gas is being passed continuously through a parallelly aligned opening via line 13. On energizing the sample inlet valve 10, the slide $10_2$ is moved laterally to align the calibrated opening containing the sample with the opening through which the carrier gas is being passed as a consequence of which the accurately measured sample is swept out of the calibrated opening and passed with the carrier gas via line 13 to column 20 for analysis.

The sample eject valve 30 is also a multi-port slide valve: and also one of a type supplied e.g. by Beckman Instruments. Its principal purpose is to allow disposal of a partially analyzed sample, once the desired portion of the analysis has been made. Forexample, if the sole objective is to analyze for water, once a water analysis of a sample has been made, the balance of the sample can be ejected from the system and vented without wasting time in analyzing for additional sample constituents in which there is no interest. The sample eject valve 30 in a de-energized mode permits continuous passage of carrier gas received from column 20, the carrier gas flowing through aligned openings within the lower portion $30_1$, slide member $30_2$ and upper portion $30_3$ of the valve body: the carrier gas entering the valve 30 via line 13 and egressing therefrom via line 15 for input into the measuring side $50_1$ of the detector 50. If, e.g., a sample is analyzed for water as the sole component of interest, after the water determination has been completed, the valve is energized, shifting the slide $30_2$ to align the opening through which the sample is carried with a vent, thereby aborting the balance of the analysis. Thereafter, the valve 30 is again de-energized and the slide $30_2$ returned to its original position in readiness for the next analysis.

The thermal conductivity detector 50 can be one of several known designs, e.g. one employed on the model 6750 Process Gas Chromatograph System manufactured and marketed by Beckman Instruments. The detector 50 is commonly manufactured and employed such that all of the elements and circuitry are housed in a single block: and although physically the detector is housed in a single metal block, it is constituted as two sides of a Wheatstone bridge circuit, a reference side $50_2$ and a measuring side $50_1$, as illustrated. A DC voltage is applied between points AB of the bridge from a thermalconductivity power supply, and an output signal is supplied between points CD of the bridge to a thermalconductivity amplifier. The detector 50 is comprised of four resistance filaments, each suspended within individual vertically oriented cavities in a metal block, and connected electrically as arms of a Wheatstone bridge. The two filaments that constitute one set of alternate arms at the measuring side $50_1$ of the bridge are positioned in an interconnected horizontally oriented passageway that receives a continuous flow of carrier gas via line 15, and carrier gas and eluting sample components on injection of a sample via actuation of the sample inject valve 10. The alternate pair of filaments constituting the second set of opposite arms of the Wheatstone bridge, providing the reference side $50_2$ of the detector 50, are positioned in an interconnected horizontally oriented passageway that receives a continuous flow of carrier gas introduced therein via line 16. In initiating a sampling operation, an appropriately adjusted, constant, voltage is first applied across the bridge, this producing an electric current which flows through the bridge filaments, heating the filaments to increase their electrical resistance. Heat is dissipated from each filament depending on the thermal conductivity of the surrounding gas. The flow of carrier gas to which water vapor has been added on passage thereof through the water vapor addition module 100 introduced via lines 15, 16, respectively, are individually regulated via adjustments of valves $15_1$, $15_2$, $16_1$ to balance the bridge. With the bridge balanced the reading for the moisture constantly and continuously added to the carrier gas by the water injection module 100 is "zero". Thereafter however, the presence of water or any other substance introduced via the sample inject valve 10 to the measuring side $50_1$ of the detector 50 will change the thermal conductivity of the gas in contact with the measuring filaments causing a difference in temperature, and therefore in resistance, between the measuring filaments and the reference filaments. The change in filament resistance unbalances the bridge, the bridge-inbalance signal is transmitted to a programmer, and processed for conveyance to the recording device wherein it can be read qualitatively and quantitatively in terms of the sample components, generally and conventionally as chromatograms.

In the practice of this invention, it is preferable to add water vapor to the total supply of the carrier gas input from the supply source to the G.C., preferably via use of the water vapor injection module 100. Preferably, the water vapor is added in constant amount, and continuously. This gas, after passage through the water vapor injection module 100, can be input via said second circuit to both the measuring side $50_1$ and reference side $50_2$ of the detector 50 and the bridge balanced, and passed simultaneously via said first circuit to wet the G.C. surfaces between the point of injection of the water-containing sample and the measuring side $50_1$ of detector 50. A water-containing sample, on injection, will then pass to the measuring side $50_1$ of detector 50 without adsorption on the surfaces and hence can be analyzed with the same effectiveness as the non-aqueous components of the sample.

The water vapor is preferably added in a constant and continuous amount. It has been found suitable to supply from about 25 parts to about 2500 parts, preferably from about 150 parts to about 1500 parts, of water vapor per million parts by weight of the carrier gas, to the carrier gas supplied to the G.C. This level of moisture in the carrier gas has been found adequate to maintain the internal walls of the G.C. sufficient to suppress the tendency of the sample moisture to wet and adhere to surfaces with which the injected moisture-containing sample is contacted, and permit proper balancing of the bridge between analyses.

It is apparent that various modifications and changes can be made, e.g. in the orientation, size, shape, layout, and in the precise character and shape of the water vapor addition module, the water permeable membrane employed therein, or the G.C. or components of the G.C., without departing the spirit and scope of the invention.

Having described the invention, what is claimed is:

1. In a gas chromatograph for identifying moisture and determining the moisture content of a water-containing sample introduced therein wherein is included, in combination carrier gas input means for the introduction and transport of carrier gas from a supply source through said gas chromatograph, a first circuit having sample injection means for intermittently introducing an accurately measured quantity of said water-containing sample into said first circuit for pick-up and transport by said carrier gas, a column, located in said first circuit downstream of said sample injection means, filled with a substrate which is contacted with carrier gas input into said first circuit of the chromatograph, and sample introduced into said first circuit of said gas chromatograph for transport by said carrier gas from which moisture can be eluted on contact with said substrate, and passed downstream via said first circuit, a thermal conductivity detector inclusive of housing means and a Wheatstone bridge housed therein, the bridge including a measuring side constituted of a pair of filaments providing a first set of opposite arms of the bridge, each positioned in a first interconnected passageway of the housing into which can be passed a continuous flow of carrier gas, and carrier gas and eluting sample components, and a reference side constituted of a second pair of filaments providing a second set of opposite arms of the bridge, each positioned in a second interconnected passageway of the housing into which can be passed a continuous flow of carrier gas, a second circuit having a flow path for conveying carrier gas from said carrier gas input means into the passageway of the housing of said detector connecting the pair of filaments constituting the reference side of said detector, and a flow path for conveying carrier gas from said carrier gas input means into the passageway of the housing of said detector connecting the pair of filaments constituting the measuring side of said detector, such that carrier gas can be introduced simultaneously into the passageways providing the pairs of filaments constituting the reference side and the measuring side, respectively, of the detector to balance the bridge, and unbalanced on introduction of the sample eluted from the column and passed thereto via said first circuit to the measuring side of the bridge to produce a bridge-inbalance signal which can be processed as output data indicative of the moisture contained in the sample, the improvement comprising water vapor addition means for introduction of water vapor into the carrier gas input means, said water vapor transported through said first circuit to the measuring side of the detector sufficient to suppress a tendency of the moisture contained in the sample to wet and adhere to surfaces with which the injected sample is contacted prior to completion of the analysis whereby, on input of the moisture-containing sample via said sample injection means for pick-up and transport by the carrier gas to the measuring side of the detector the output signal for the water content of the sample can be easily read with precision and accuracy.

2. The apparatus of claim 1 wherein water vapor is added by the water vapor addition means to the total of the carrier gas input into the gas chromatograph, and the carrier gas which contains the water vapor is input into both the first circuit and second circuit of the gas chromatograph.

3. The apparatus of claim 1 wherein the first circuit additionally includes sample eject means in said first circuit downstream and in series with the column so that after completion of the initial portion of the analysis the balance of the sample can be discharged from said first circuit to by-pass the measuring side of the detector.

4. The apparatus of claim 1 wherein the water vapor addition means is constituted of a water supply vessel having a water outlet, a membrane housing, formed by an enclosing wall, contiguous to said water supply vessel which has a chamber with a carrier gas inlet for admitting carrier gas into the chamnber, a carrier gas outlet for passing carrier gas from the chamber, and water inlet in communication with said water outlet of said water supply vessel, and a water permeable membrane located between the water outlet of said water supply vessel and water inlet of said membrane housing through which water can be supplied by said water supply vessel into the chamber of said membrane housing for pickup of water as a vapor by carrier gas passed via said carrier gas inlet into said chamber, and passed via said carrier gas outlet from the chamber of said membrane housing.

5. The apparatus of claim 4 wherein the water outlet of the water supply vessel is supplied via a tubular section to the upper surface of the membrane as a liquid interface, the tubular section is threadably engaged to the wall of the membrane housing, the membrane rests atop a washer provided with a central opening, and both the membrane and washer are supported upon the wall of the membrane housing.

6. The apparatus of claim 5 wherein the central opening of the membrane is sized in relation to the permeability of the membrane, and the carrier gas is passed continuously at a constant rate of flow through the chamber sufficient to supply from about 25 parts to about 2500 parts of water vapor per million parts by weight of the carrier gas, to the carrier gas passed via said carrier gas outlet from said membrane housing.

7. The apparatus of claim 6 wherein from about 150 parts to about 1500 parts of water vapor is supplied to the carrier gas passed via said carrier gas outlet from said membrane housing.

8. The apparatus of claim 4 wherein the membrane is constituted of a perfluorosulfonate ionomer.

9. In a gas chromatograph for identifying moisture and determining the moisture content of a water-containing sample wherein is included, in combination, carrier gas input means for input and transport of carrier gas from a supply source through a gas chromatograph, sample injection means for introducing an accurately measured quantity of said water-containing sample into said gas chromatograph for pick-up and transport by said carrier gas, a column located downstream of said sample injection means which is filled with a substrate which is contacted with carrier gas input into the chromatograph, and sample introduced into said gas chromatograph for transport by said carrier gas and from which moisture can be eluted on contact with said substrate, a thermal conductivity detector inclusive of housing means and a Wheatstone bridge housed therein, the bridge including two pairs of filaments, each pair of filaments being positioned within an interconnected passage contained in said housing means, and each pair of filaments constituting a set of opposite arms of said bridge such that carrier gas can be flowed through the passages across each pair of the filaments to provide a measuring side and a reference side, respectively, and the bridge balanced, and unbalanced on introduction of eluting sample from the column to the measuring side of the bridge to produce a bridge-inbalance signal which can be processed as output data indicative of the moisture contained in the sample, the improvement comprising water vapor addition means for the introduction of water vapor into the carrier gas input means, said water vapor transported to both the measuring side and the reference side of the detector, and to the carrier gas input means to the sample injection means and column, sufficient to suppress tendency of the moisture contained in the sample to wet and adhere to gas chromatograph surfaces with which the injected sample is contacted prior to completion of the analysis whereby, on input of the moisture-containing sample via said sample injection means for pick-up and transport by the carrier gas to the measuring side of the detector, the output signal for the water content of the sample can be easily read with precision and accuracy.

* * * * *